United States Patent [19]

Miller

[11] Patent Number: 5,318,566
[45] Date of Patent: Jun. 7, 1994

[54] STERNOTOMY CABLE AND METHOD
[75] Inventor: David F. Miller, Memphis, Tenn.
[73] Assignee: Danek Medical, Inc., Memphis, Tenn.
[21] Appl. No.: 901,926
[22] Filed: Jun. 22, 1992
[51] Int. Cl.⁵ .............................................. A61B 17/00
[52] U.S. Cl. ....................................................... 606/60
[58] Field of Search ................. 606/53, 60, 103, 139, 606/151, 157, 222, 223, 224, 225, 226, 227, 228, 232, 233; 24/28, 29, 131 R

[56] References Cited

U.S. PATENT DOCUMENTS

| | | |
|---|---|---|
| 3,125,095 | 3/1964 | Kaufman et al. . |
| 3,311,110 | 3/1967 | Singerman et al. . |
| 3,910,282 | 10/1975 | Messer et al. . |
| 4,201,215 | 5/1980 | Crossett et al. ................ 606/151 X |
| 4,512,346 | 4/1985 | LeMole . |
| 4,535,764 | 8/1985 | Ebert .............................. 606/224 X |
| 4,583,541 | 4/1986 | Barry . |
| 4,730,615 | 3/1988 | Sutherland et al. . |
| 4,802,477 | 2/1989 | Gabbay . |
| 4,896,668 | 1/1990 | Popoff et al. . |
| 4,901,721 | 2/1990 | Hakki . |
| 4,944,753 | 7/1990 | Burgess et al. ................. 606/86 X |
| 4,966,600 | 10/1990 | Songer et al. . |
| 5,089,012 | 2/1992 | Prou ................................... 606/224 |

OTHER PUBLICATIONS

"Danek Songer Cable System" flyer form No. LIT--SONG Feb. 1 1990, published by Danek Medical Inc., 3092 Directors Row, Memphis, TN, 38131.

Primary Examiner—Robert A. Hafer
Assistant Examiner—Sam Rimell
Attorney, Agent, or Firm—Woodard, Emhardt, Naughton, Moriarty & McNett

[57] ABSTRACT

A curved needle with a flexible leader wire and a multi-stranded cable fastened to the leader wire is passed through one half of a vertically split sternum from in front of the one half of the sternum to the back of the one half and then across behind the sternum to the back of the other half of the sternum and then forward to a location in front of the other half of the sternum. A crimp on the trailing end of the cable abuts one side of a stop bar in front of the sternum. The needle and other end of the cable are passed from the other side of the bar through an aperture in the bar. The needle is then separated from the leader. This procedure is repeated at the desired number of vertically spaced sites on the sternum. Then the sternum halves are brought together. Each of the cables is tensioned to hold the sternum together, and a crimp is swaged onto the cable at the other side of the bar whereby the crimp holds the cable in tension. Then the extra cable is cut off.

7 Claims, 2 Drawing Sheets

U.S. Patent    June 7, 1994    Sheet 1 of 2    5,318,566
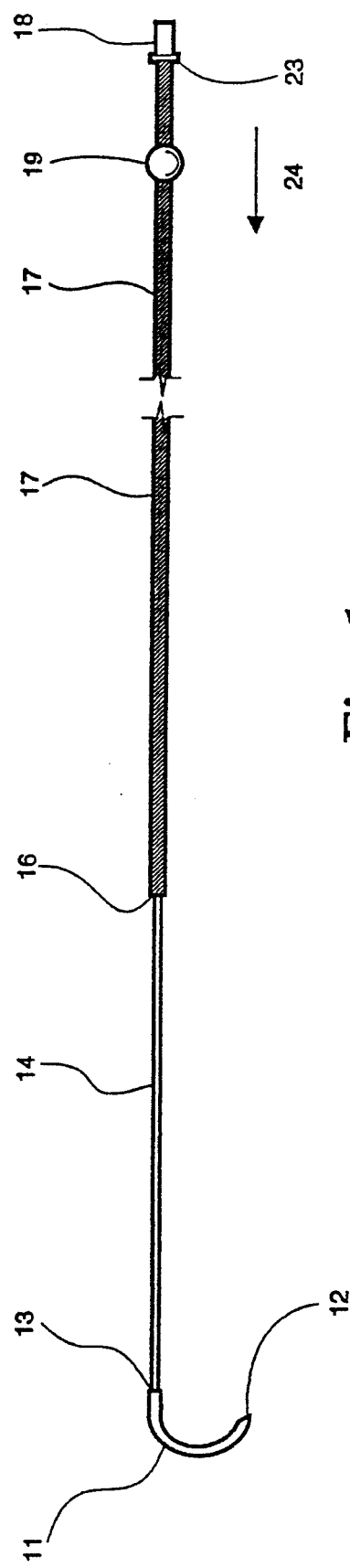
Fig. 1
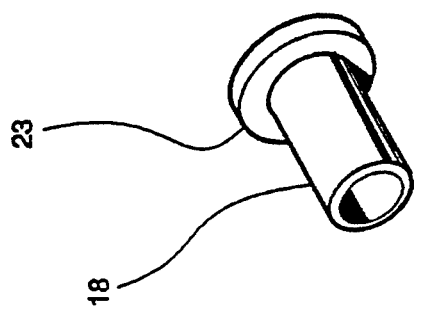
Fig. 3
Fig. 2

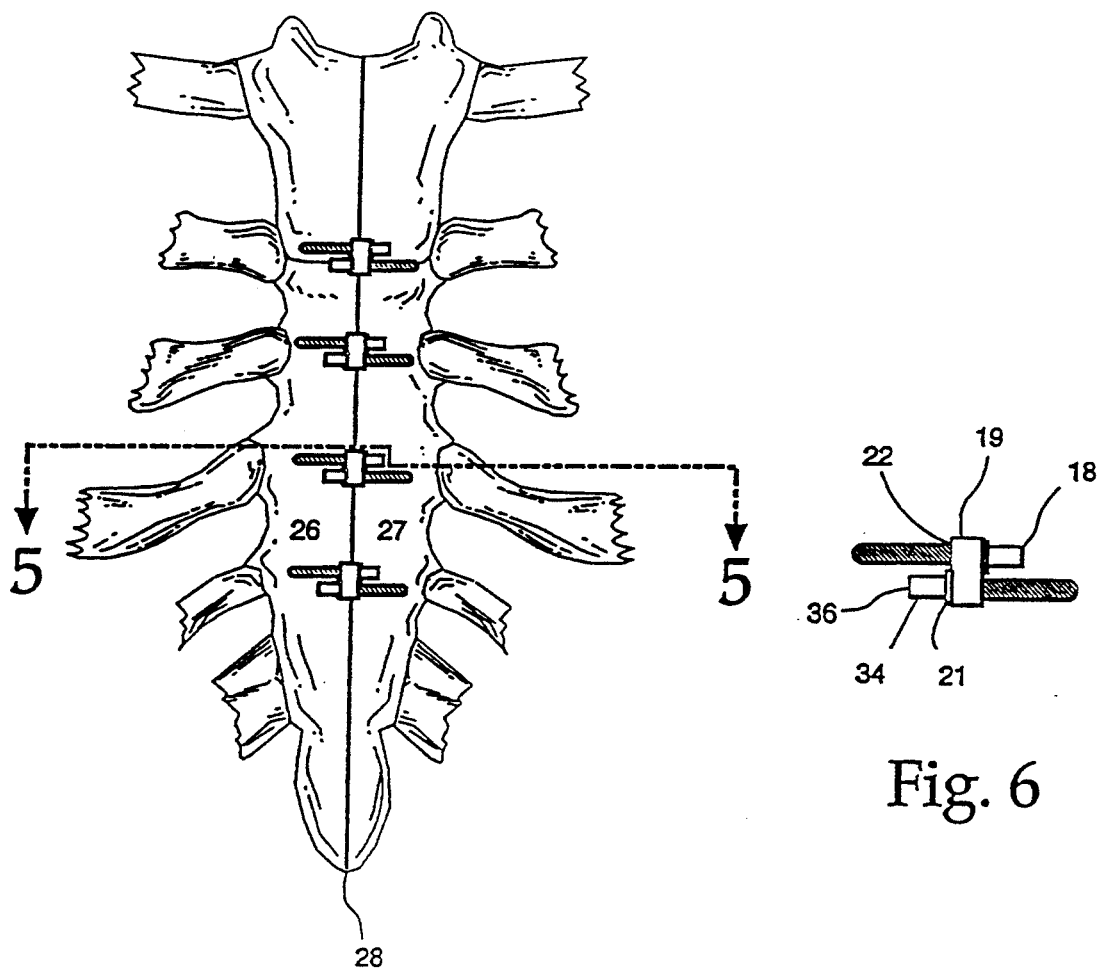
Fig. 4
Fig. 6
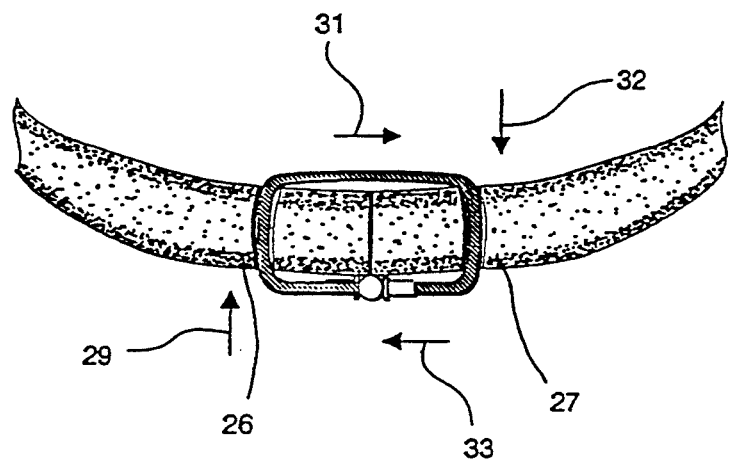
Fig. 5

STERNOTOMY CABLE AND METHOD

BACKGROUND OF THE INVENTION

1. Field of the Invention

This invention relates generally to orthopedic surgery, and more particularly to a cable system and method for closing the sternum after open heart surgery or a similar procedure.

2. Description of the Prior Art

For major thorasic surgery, such as open heart surgery, for example, the sternum is split from top to bottom to provide access to the organs in the thorasic cavity. Following the surgical procedure within the cavity, it is necessary to close and secure the sternum for healing. One procedure for doing this involves the making of pairs of holes in the sternum, one hole of the pair in each of the severed sides of the sternum. The hole pairs are in vertically spaced locations. A surgical wire is passed through the two holes of each pair, pulled tight to join the two halves of the sternum, and twisted together to stay tight.

Another procedure intended to better distribute the forces of the wires is disclosed in U.S. Pat. No. 4,512,346 to LeMole. In that disclosure, rods 16a and 16b located on the posterior surfaces of the sternum are used as anchors for surgical wires which are then pulled and twisted together to hold the sides of the sternum together for healing.

Another system disclosed in U.S. Pat. No. 4,583,541 to Barry uses wires through vertically spaced pairs of holes in the sides of the sternum and which match the vertically spaced pairs of holes in a strap located at the front of the sternum and through which the wires are received and then the wires are twisted together. The knots are received in a vertically extending groove in the strap.

Another system is disclosed in U.S. Pat. No. 4,730,615 to Sutherland et al, and employs a needle with an attendant metal spine portion 14 and a so-called head portion 12. The needle is the end of the spine portion and sharpened so that it can be pushed through intercostal tissue along the outer edge of the sternum, from outside toward the internal body cavity, and then pulled back out from behind the other half of the sternum. Then the locking serrations are pulled through the head portion 12 whereupon, when sufficient tension is applied, the locking of the appropriate serration with the tang 30 in the head portion will retain the fastener in place. Then the needle and excess metal spine portion are cut off.

Another approach is shown in U.S. Pat. No. 4,802,477 issued Feb. 7, 1989 to Gabbay.

Another approach is disclosed in U.S. Pat. No. 4,896,668 issued to Popoff et al. and wherein a vertically extending sternum plate is provided behind the sternum and receives a wire through it whose ends are secured in front of the sternum.

A U.S. Pat. No. 4,901,721 issued Feb. 20, 1990 to Hakki discloses a suturing device for cardio thorasic surgery The Singerman et al. U.S. Pat. No. 3,311,110 issued Mar. 28, 1967 shows an earlier surgical needle and suture wire arrangement.

There is a system known as the Songer Cable System employed in orthopedic surgery. The cable typically comprises a bundle of forty-nine strands of wire. The cable is an eighteen gauge cable with a "top-hat" type of crimp thereon at the cable ends when fixed in site. The material used for the cable and crimp is 316 LVM stainless steel. One type uses a solid stainless steel cylindrical bar having two transverse holes drilled through it perpendicular to its longitudinal axis. The cable is threaded through one hole in the bar, and then around the device or structure to be secured, and then through the other hole in the bar. Tools are used for the functions of tensioning the cable and swaging crimps into place on the cable for abutting contact with the bar to maintain tension in the cable. U.S. Pat. No. 4,966,600 issued Oct. 30, 1990 to Songer et al. discloses and explains details of a Songer system.

SUMMARY OF THE INVENTION

According to a typical embodiment of the invention, a curved needle is used with one end of a flexible suture wire leader secured by a swiveling swage to the unpointed end of the needle, and a multi-stranded cable fastened to the other end of the leader. A stop is fixed to the free end of the cable. An abutment which is slidable on the cable is located adjacent the stop. The curved needle is passed through the sternum from in front of one side of the sternum to the back of the one side and then across to the back of the other side of the sternum and then forward to a location in front of the other side of the sternum. The leader and cable are thereby pulled along the path of the needle until the stop on the trailing end of the cable is located in front of the sternum. The needle is snapped or cut from the leader, and the leader is pushed through a hole in the abutment. The leader is followed through the hole by the cable until the stop at the trailing end of the cable engages the abutment in front of the sternum. Then the remaining leader is passed through the aperture in another stop which is slidably moved to the abutment side opposite the first stop. After this is done at several sites up and down the sternum, the sternum sides are brought together and a suitable amount of tension is applied to the cables to pull and hold the two sides of the sternum snugly together. Then the second stop on each cable is butted against the abutment and affixed to the cable to hold the tension.

BRIEF DESCRIPTION OF THE DRAWINGS

FIG. 1 is a top plan view of a sternotomy cable according to a typical embodiment of the present invention.

FIG. 2 is an enlarged pictorial view of an abutment stop bar used on the cable.

FIG. 3 is an enlarged pictorial view of a stop crimp used on the end of a cable.

FIG. 4 is a fragmentary front elevational view of a sternum held in position to heal by the sternotomy cable installed according to the present invention.

FIG. 5 is a fragmentary cross sectional view through the sternum at line 5—5 in FIG. 4 and viewed in the direction of the arrows.

FIG. 6 is an enlarged front elevational view of a cable termination as in FIG. 4.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, a crescent shaped sternotomy surgical needle 11 has a pointed distal end 12, and a proximal end 13 fastened by a swivel swage to the end of a surgical wire 14 which serves as a leader and is welded at 16 to a multi-stranded cable 17. A "top hat" crimp 18 is swaged to the end of the cable 17. An abutment stop bar 19 has two apertures 21 and 22 (FIG. 2) therein, one of which (22, for example) receives the cable 17 through it initially. The aperture is large enough to slidingly receive the cable through it but small enough to enable the flange 23 on the crimp 18 to bear on the cylindrical wall of the bar 19 when the cable is pulled in the direction of arrow 24 as the bar is held stationery until abutment of the flange 23 with the right-hand side of the bar. The needle and leader wire may be a pre-assembled unit with the leader wire being monofilament stainless steel suture wire of approximately three inch length between the proximal end of the needle and the end welded to the cable. The cable itself is comprised of a tightly wound bundle of seven bundles of seven wires each of 0.005 inches diameter. The cable is preferably 18 inches long and drawn from an outside diameter of 0.045 inches to 0.041 inches. The end stop 18 is preferably crimped in a hexagonal die to 0.068 inches across the flats of the hex. The abutment bar 19 is slided onto the cable before the leader 14 is welded to cable 17 at the uncrimped cable end 16.

The material of the wires in the cable and the bar and the crimp is No. 316LVM stainless steel. The needle and monofilament leader may be of the same material or other suitable material known in the art.

In the use of the cable according to the present invention, and referring to FIGS. 4 and 5, the two sides of the sternum are shown at 26 and 27, the sternum having been split into two halves 28. With the thoracic surgery completed, the sternum sides can be brought together at the split to be held there by a set of cables installed according to this invention. For that purpose, and relating FIG. 1 to FIG. 4, it will be assumed that the surgeon begins with the needle at the left-hand side of the cable as shown in FIG. 1, whereupon the surgeon inserts the needle into and through the cortical, cancellous and cortical bone structure in succession in the sternum side 26 in the direction of arrow 29 Then the needle is moved across the space between the sternum sides in the direction of arrow 31 to the back of sternum side 27 whereupon the needle is inserted through the bone in the forward direction of arrow 32 and exits at the front of the sternum side 27. During this operation, the leader wire and cable is drawn through the holes in the sternum halves that have been made by the needle. Then the needle is cut or snapped off the leader wire 14 and, assuming that the cable 17 originated in the hole 22 in the bar 19, the leader wire is passed through the hole 21 in the direction of arrow 33. The crimp 34 which is originally identical to crimp 18, for example, is then installed on the leader wire and pushed up against the bar 19 at the hole 21.

After this procedure has been followed at additional vertically spaced locations on the sternum, (usually five to seven, although only four are shown for convenience herein) the number depending upon the circumstances of the particular case involved, the sternum sides are brought together. Then a tensioning tool and crimping tool or a combination crimper/tensioner tool can be applied to the cable and the crimp at each site to pull the cable to the desired tension and then swage the crimp 34 onto the cable with the crimp flange tight against the bar 19 so that, when the tensioner is removed from the cable, the cable will remain in tension and holding the two sternum sides 26 and 27 tightly together in abutting relation at the split 28. Then, the extra cable with leader thereon which extends beyond the end 36 of the crimp 34 is cut off at the end 36 to complete the procedure. The amount of tension applied to the cable, and the determination of whether the needle is to be used through the the sternum itself as described here, or through cartilage or muscle in the intercostal space between ribs, as well as other details, will be based upon the judgment of the operating surgeon considering the circumstances of the case.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. Sternotomy closure apparatus comprising:
   a curved needle having two ends, with a point at one end for piercing animal tissue, and a connection to a flexible leader at the other end;
   a flexible leader having two ends, the leader having one end connected to the other end of the needle;
   a flexible multi-strand cable having two ends;
   a stop on one end of the cable, the other end of the cable being attached to the other end of the leader; and
   an apertured bar on the cable at the stop.

2. The apparatus of claim 1 and wherein:
   the bar has two apertures therein, the cable being received through one of the apertures, the other aperture being sized to fittingly receive the cable through it.

3. Sternotomy closure comprising:
   a flexible multi-strand cable for extending across behind the junction of two halves of a longitudinally split sternum, and the forward around portions of each half of the sternum to the front of the sternum and pulling the two halves of the sternum together, the cable having two end portions and ends;
   an apertured bar on the cable receiving the end portions of the cable through the bar;
   two crimps, one of the crimps being fixed on each end portion of the cable adjacent the end of the cable, the crimps being abuttingly engaged with the bar and maintaining position of the cable ends relative to each other to thereby hold the two halves of the sternum together at the junction for healing;
   the crimps having a tubular portion with a flange at one end radially extending from the tubular portion;
   the tubular portions being swaged onto the cable at the end of the cable; and
   the bar being mounted on the cable between the flanges of the crimps and gripped between the flanges.

4. A method of securing closed for healing, a sternum which has been split into two halves, and comprising the steps of:
   a. passing a needle from in front of one side of the sternum to the back of the one side and then across to the back of the other side of the sternum and then forward to a location in front of the other side of the sternum;
   b. pulling a multi-stranded cable along the path of the needle until a trailing end of the cable is stopped in front of the sternum;
   c. pulling a length of the cable through a hole in a stop member;
   d. closing the two halves of the sternum together at the split for healing;
   e. applying tension to the cable to hold the two halves of the sternum together; and
   f. fixing to the cable, means to hold the cable.

5. The method of claim 4 and wherein:
   steps a., b., and c. are performed at a plurality of locations longitudinally of the sternum before step d.; and
   steps e. and f. are performed at the locations after step d.

6. The method of claim 4 and wherein the step of fixing further comprises the steps of:
   placing an abutment member located on the cable at a stop fixed to the trailing end of the cable;
   locating a crimp on the cable at the abutment member;
   swaging the crimp to the cable while the crimp is abuttingly engaging the abutment member and the abutment member is abuttingly engaging the stop.

7. The method of claim 6 and further comprising the step of:
   cutting the cable at the crimp.

* * * * *